(12) United States Patent
Krueger et al.

(10) Patent No.: US 8,492,709 B2
(45) Date of Patent: Jul. 23, 2013

(54) METHOD AND APPARATUS FOR CHEMICAL AND BIOLOGICAL SAMPLE SEPARATION

(75) Inventors: Clinton Alawn Krueger, Milton, MA (US); Ching Wu, Acton, MA (US); Christopher K Hilton, Acton, MA (US)

(73) Assignee: Excellims Corporation, Acton, MA (US)

( * ) Notice: Subject to any disclaimer, the term of this patent is extended or adjusted under 35 U.S.C. 154(b) by 0 days.

(21) Appl. No.: 13/544,811

(22) Filed: Jul. 9, 2012

(65) Prior Publication Data

US 2012/0273667 A1 Nov. 1, 2012

Related U.S. Application Data

(63) Continuation of application No. 12/577,062, filed on Oct. 9, 2009, now Pat. No. 8,217,338.

(60) Provisional application No. 61/104,319, filed on Oct. 10, 2008.

(51) Int. Cl.
*B01D 59/44* (2006.01)
*G01N 27/64* (2006.01)
*H01J 49/34* (2006.01)

(52) U.S. Cl.
USPC ............ 250/282; 250/281; 250/284; 250/288

(58) Field of Classification Search
USPC ....................................................... 250/282
See application file for complete search history.

(56) References Cited

U.S. PATENT DOCUMENTS

| 7,015,462 | B2 * | 3/2006 | Karas ............................. 250/287 |
| 7,348,184 | B2 * | 3/2008 | Rich et al. ...................... 436/518 |
| 7,645,584 | B2 * | 1/2010 | Svetlov et al. .................. 435/7.1 |
| 7,709,788 | B2 * | 5/2010 | Geraghty et al. .............. 250/282 |
| 8,022,359 | B2 * | 9/2011 | Michelmann ................. 250/282 |
| 2010/0127166 | A1 * | 5/2010 | Krueger et al. ............... 250/282 |
| 2010/0148058 | A1 * | 6/2010 | Krueger et al. ............... 250/282 |

* cited by examiner

*Primary Examiner* — David A Vanore

(57) ABSTRACT

The present invention describes a method and apparatus for separating chemical and/or biological samples based on selective ion-molecular interactions in the gas phase. A chemical modifier is added to the drift gas that interacts selectively with a targeted molecule in at least one component of the sample in a drift tube. The component may be impurities and/or interferences in the sample whereby the chemical modifier enhances sample resolution by shifting the components drift times. In addition, reagents can be added to the sample prior to, during, or after ionization to form a complex with selected components in the sample. In addition, one or more internal and/or external standard can also be added to the sample as a calibration for the measurement.

20 Claims, 10 Drawing Sheets

R = *i*-Pr, Et, Me, *t*-Bu, n-Bu, n-Pr

R = *i*-Pr, Et, Me, *t*-Bu, n-Bu, n-Pr

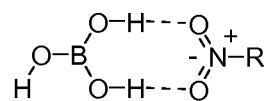
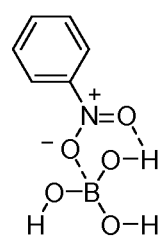
Figure 7
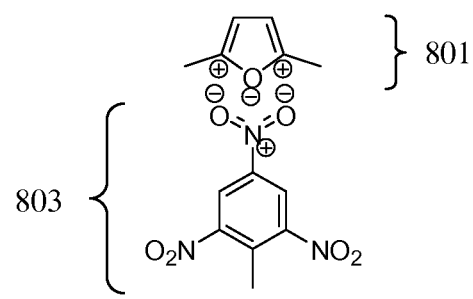
Figure 8

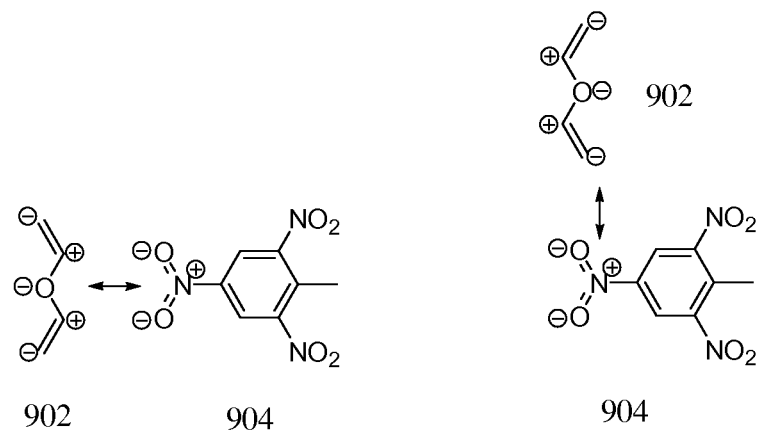
Figure 9A                     Figure 9B
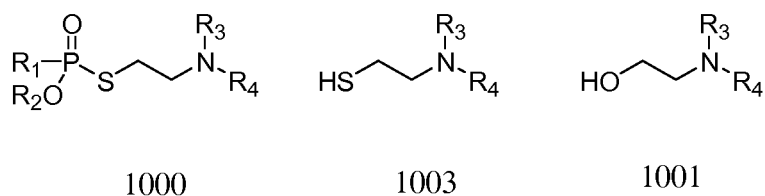
Figure 10
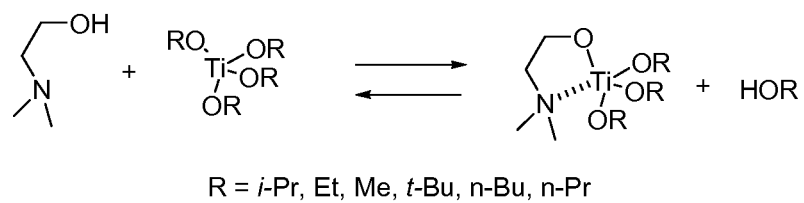
R = *i*-Pr, Et, Me, *t*-Bu, n-Bu, n-Pr
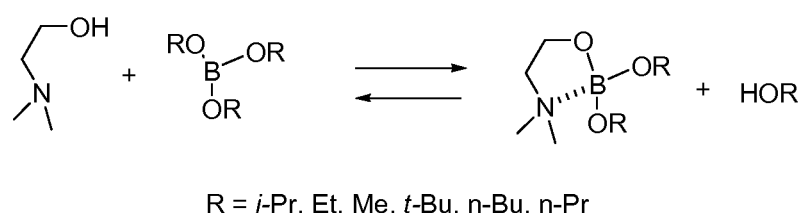
R = *i*-Pr, Et, Me, *t*-Bu, n-Bu, n-Pr
Figure 11

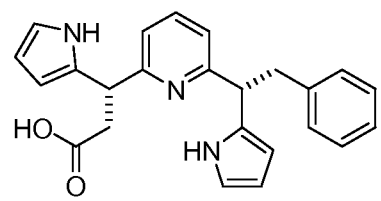
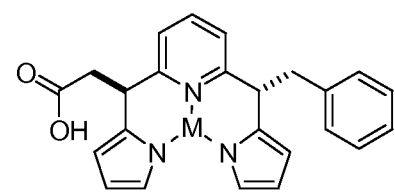
Figure 15A        Figure 15B
Figure 16

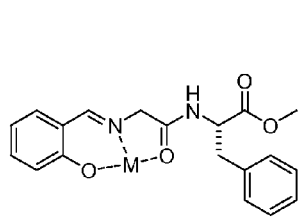 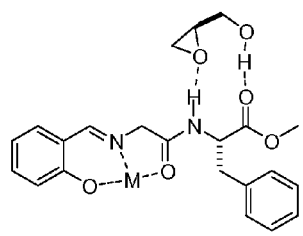 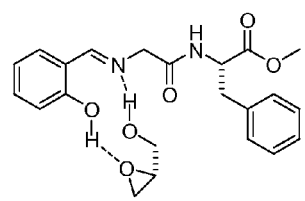
Figure 17A　　　　　　　Figure 17B　　　　　　　Figure 17C
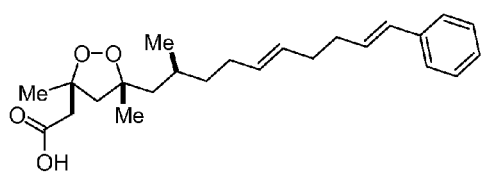 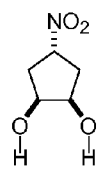 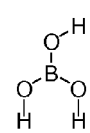
1801　　　　　　　　　　1803　　　　　　　1805
Figure 18
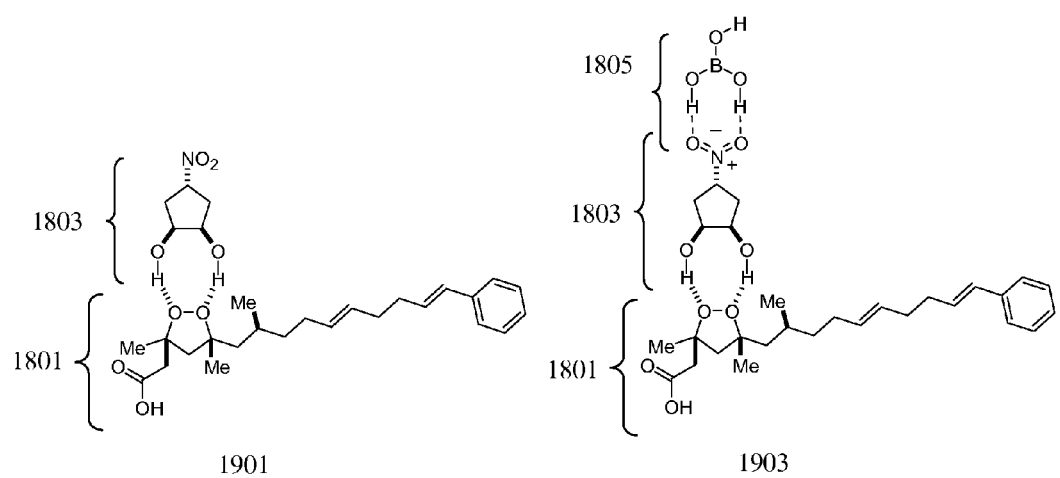 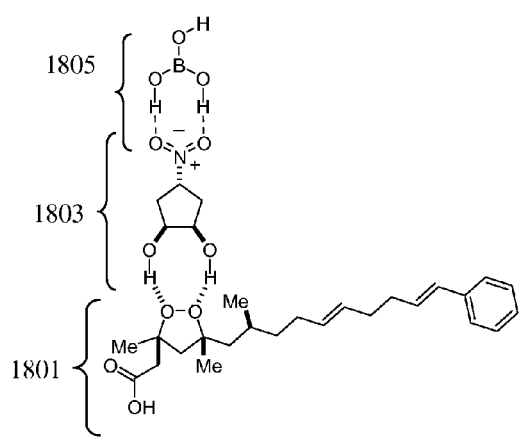
1901　　　　　　　　　　　　　　1903
Figure 19

ND APPARATUS FOR CHEMICAL
METHOD AND APPARATUS FOR CHEMICAL AND BIOLOGICAL SAMPLE SEPARATION

CROSS-REFERENCE TO RELATED APPLICATIONS

This application is a continuation of U.S. patent application Ser. No. 12/577,062, filed Oct. 9, 2009, the entire content of which is herein incorporated by reference. The present application claims the benefit of and priority to corresponding U.S. Provisional Patent Application No. 61/104,319, filed Oct. 10, 2008, the entire content of which is herein incorporated by reference.

BACKGROUND OF THE INVENTION

Ion mobility spectrometers (IMS) have become a common tool for detecting trace amounts of chemical and/or biological molecules. Compared to other spectrometric chemical analysis technologies, e.g., mass spectrometry, IMS is a relatively low resolution technique. The IMS advantages of very high sensitivity, small size, low power consumption, and ambient pressure operation are in some cases completely offset, or at a minimum, reduced by the lack of sufficient resolution to prevent unwanted responses to interfering chemical and/or biological molecules. The false positives that result can range from minor nuisances in some scenarios to major headaches in others. Interfering chemical and/or biological molecules can have very similar ion mobilities which in turn can significantly limit detecting and identifying low levels of the targeted chemical and/or biological molecules in the sample.

Another IMS resolution issue can occur as the molecules increase in molecular complexity (size, number of stereogenic centers, number of chiral centers, number of functional groups, etc). More conformations are possible due to the flexibility of the molecule, which can thus adopt multiple different conformations while traveling down the drift tube.

The present state of the art ion mobility spectrometers lack the ability to: directly reduce the occurrence of interfering chemical and/or biological molecules in a sample's analysis, limit the number of possible conformations of a molecule, and report the relative difference of a molecule to an internal standard. The molecular geometry of molecules can be utilized in the efforts to explore new analytical spectroscopic/spectrometric techniques. It is the purpose of this invention to overcome these obstacles by making the use of a molecule's molecular geometry.

SUMMARY OF THE INVENTION

In one aspect of the present invention, at least one chemical modifier is added to the drift gas that interacts selectively with a targeted molecular geometry in at least one component of the sample in a drift tube. The component may be impurities (impurity) and/or interferences (interference) in the sample whereby the chemical modifier enhances sample resolution by shifting the components drift times. The chemical modifier interaction forces, may include hydrogen bonding, dipole-dipole, and steric hindering effects, but are not limited to only these. In addition, at least one metal and/or other reagent can be added to the sample prior to, during, or after ionization to form a complex with: either the targeted chemical and/or biological molecules or the impurities and/or interferences in the sample, or both. In addition, one or more internal and/or external standard can also be added to the sample to generate a reference for measurement.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIG. 7 shows multiple interaction points between boric acid and nitro compounds.

FIG. 8 shows a dipole-dipole interaction of 2,5-Dimethylfuran and TNT.

FIGS. 9A-B shows two possible manners in which divinyl ether interacts with TNT.

FIG. 10 shows two possible degradation products of the VX/V-type nerve agent.

FIG. 11 shows the reversible interactions of $Ti(OR)_4$ and $B(OR)_3$ with bidentate ligands.

FIGS. 15A-B shows a unrestricted molecule with 2 chiral centers 15A and a metal bound complex 15B.

FIG. 16 shows a molecule with one chiral center.

FIGS. 17A-C shows different interactions with the molecule.

FIG. 18 shows a biologically active peroxide, a transforming agent, and a chemical modifier.

FIG. 19 shows the chemical modifier bound selectively to the complex 1901 through the nitro functionality found on the transforming agent 1803 as complex 1903.

DETAILED DESCRIPTION OF VARIOUS EMBODIMENTS

Figure 1:
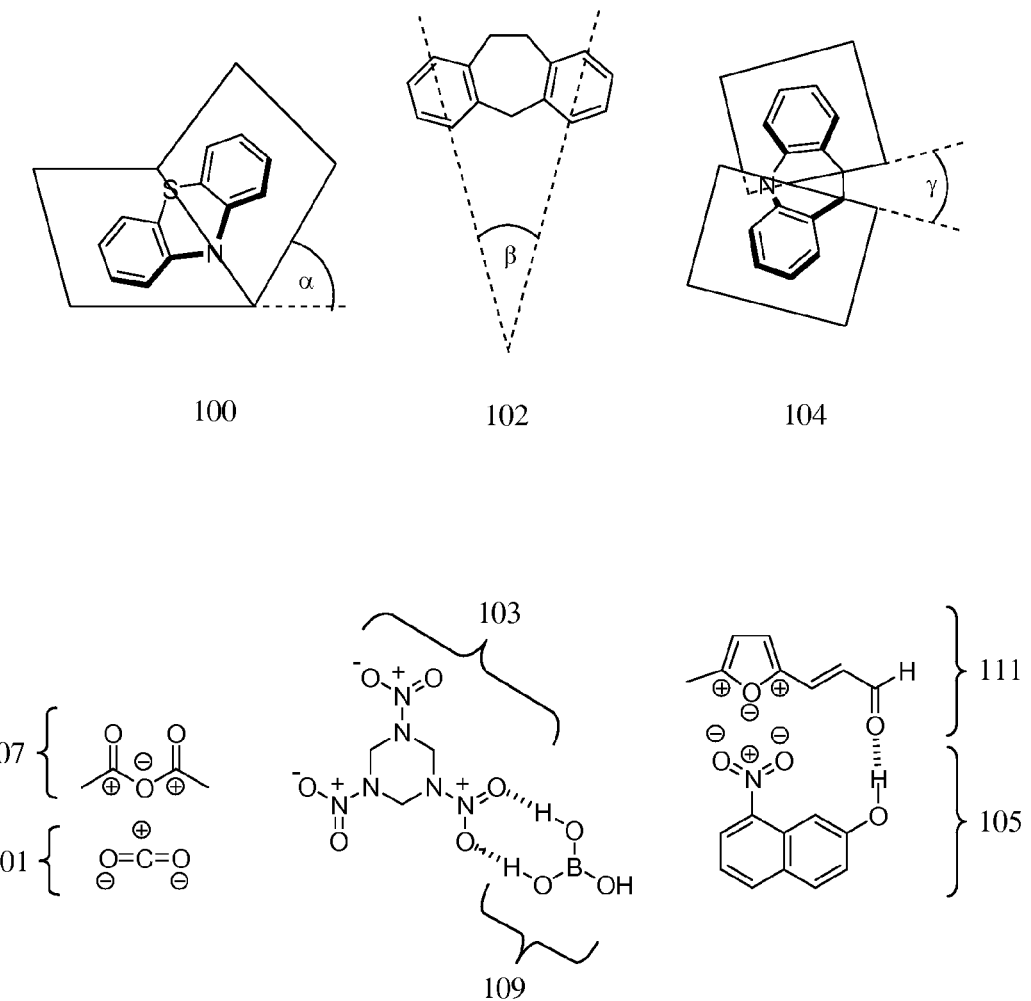
FIG. 1 shows the molecular geometry of a molecule may be due to the molecules' ring topology, from one or more of the functional groups found in the molecule, or may be part of the entire molecule.

Unless otherwise specified in this document the term "ion mobility based spectrometer" is intended to mean any device that separates ions based on their ion mobilities and/or mobility differences under the same or different physical and/or chemical conditions, the spectrometer may also include detecting the ions after the separation process. Many embodiments herein use the time of flight type IMS as examples; the term ion mobility based spectrometer shall also include many other kinds of spectrometers, such as differential mobility spectrometer (DMS) and field asymmetric ion mobility spectrometer (FAIMS), and other derived and/or combined forms of spectrometers. Unless otherwise specified, the term ion mobility spectrometer or IMS is used interchangeable with the term ion mobility based spectrometer defined above.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "chemical and/or biological molecule" is intended to mean single or plurality of particles that are, either charged or not charge, derived from atoms, molecules, particles, and subatomic particles.

In one aspect of the present invention, at least one chemical modifier is added to the drift gas that interacts selectively with a targeted molecular geometry in at least one component of the sample in a drift tube. The sample may comprise explosives, chemical warfare agents, toxic industrial chemicals, toxins, biological warfare agents and/or other chemical, biological compounds. The component of the sample can be: a chemical and/or biological molecule that is of interest or the component may be impurities and/or interferences in the sample whereby the chemical modifier enhances sample resolution by shifting the components drift times. By utilizing the components' molecular geometry, the chemical modifier interacts preferentially with one component over another through an ion-molecular interaction. The chemical modifier interaction forces, may include; hydrogen bonds, van der Waals forces, dipole-dipole, steric hindering effects, coordinate covalent bond, metallic bond, ionic bond, non-covalent bond, weak covalent nature, antibonding, but is not limited to only these. The chemical modifier interaction forces may also include the formation of short-lived metastable compounds and/or clusters. The clusters can be long-lived non-covalent interactions or covalent interactions.

A structure selective resolution method can comprise of:providing a sample with at least one component having a targeted molecular geometry to an ion mobility based spectrometer; ionizing the sample; adding at least one chemical modifier having a complementary molecular geometry that interacts selectively with the targeted molecular geometry of said at least one component of the sample; and resolving at least one component from the other components of the sample based on their measured ion mobility characteristics. The measured ion mobility characteristic can be a measured drift time of the components. The measured ion mobility characteristic can be the ion flight path under influence of high field and/or low field conditions in an ion mobility base spectrometer. The component of the sample that the chemical modifier interacts preferentially with can be a impurity(ies) and/or interference(s) in the sample.

In another aspect of the present invention, the chemical modifier can be added to the sample prior to ionization and/or directly introducing them into the ionization source, reaction region, drift region of the drift tube of time of flight type of IMS. In case of other type of ion mobility based spectrometer, the modifier could be added into the carrier gas before or during separation.

Molecular geometry or molecular structure is the three dimensional arrangement of the atoms that constitute a molecule. The molecular geometry of a molecule can be used to help make predictions about crystal structure, dipole moment, reactivity, bond lengths, bond angles, to name a few. There are six basic geometrical shapes for small molecules and/or individual functional groups: linear (planar), trigonal planar, tetrahedral, octahedral, pyramidal, and bent. Larger molecules often have a unique topology that is established by one or more functional groups and/or the core shape of the molecule that gives rise to their molecular geometry. This unique topology can arise from the fact that each atom within a molecule occupies a certain amount of space, i.e. steric effect and elicit a specific steric attraction. Steric attraction occurs when molecules have geometries that are optimized for interaction with one another. In these cases molecules will react/interact with each other most often in specific arrangements. A non-limiting example of a larger molecule with a specific topology arises from the core shape of the molecule is shown in FIG. 1. The α angle of molecule 100, the β angle of molecule 102, and the γ angle of molecule 104 gives rise to a ring topology that is unique. As shown in FIG. 1, the molecule's geometrical shape may be part of the entire molecule, such as carbon dioxide 101 (linear geometry), or may be from one or more of the functional groups found in the molecule, such as the nitro functional group found in cyclotrimethylenetrinitramine (RDX) 103 (trigonal planar geometry). In addition, different functional group combinations within a molecule can set up a molecules' molecular geometry, such as 1-nitro-7-naphthol 105. Each functional group's atoms and hybridization establishes the molecules' unique molecular shape. The molecular geometry of each functional group can be used to elicit specific ion-molecular interactions with a chemical modifier. The chemical modifier's molecular geometry would need to be complementary to the component to be separated/resolved molecular geometry. For example, since carbon dioxide (component to be separated/resolved) 101 has a linear geometry, a chemical modifier that also displays a linear geometry would be necessary for a dipole-dipole ion-molecular interaction to take place. Although the point charges are not exactly in a linear geometry for acetic anhydride (chemical modifier) 107, the molecular geometry may be good enough to induce a force between the two molecules 101 and 107. If the targeted molecular geometry of RDX 103 is one of the three nitro functional groups, then a chemical modifier would need to meet these geometrical requirements by having a complementary molecular geometry. The nitro group has a trigonal planar geometry, therefore boric acid 109 would be a good choice for a chemical modifier because of boric acid's trigonal planar geometry. The ion-molecular interaction between these two molecules 103 and 109, is through hydrogen bonding. Different functional group combinations within a molecule set up a molecules' geometric frame, such as 1-nitro-7-naphthol 105. A nitro group along with an alcohol functional group in the same molecule with an aromatic napthyl ring core sets an overall planar molecular geometry. A chemical modifier with a planar geometric frame, such as molecule 111 may be advantageous to exploit a dipole-dipole interaction with the nitro group functionality along with a hydrogen bonding interaction with the alcohol functional group.

Functional groups are specific groups of atoms within molecules that are responsible for the characteristic interaction of these molecules in chemical reactions (forming and breaking of chemical bonds) and attraction forces. The molecular shape of the molecules are dictated by the combinations and locations of the functional groups that make up a molecule's geometric frame and therefore influence the molecules interactions between molecules. These interactions or attraction forces may include; hydrogen bonds, van der Waals forces, dipole-dipole, steric hindering effects, coordinate covalent bond, metallic bond, ionic bond, non-covalent bond, covalent bond, weak covalent nature, antibonding, short-lived metastable, clusters, but is not limited to only these. The clusters can be long-lived non-covalent interactions or covalent interactions.

As used herein, the term "functional group" may include the following specific groups of atoms within molecules; acetal, acetoxy group, acetyl, acid anhydride, acryl group, acyl, acyl halide, acylal, acyloin, acysilane, alcohol, aldehyde, aldimine, alkane, alkene, alkoxide, alkoxy group, alkyl, alkyl cycloalkane, alkyl halide, alkyl nitriles, alkyne, allene, allyl, amine, amide, amidine, amine oxide, amino, ammonium, amyl, aryl, azide, aziridine, azo compound, azoxy, benzoyl, benzyl, beta-lactam, bisthiosemicarbazone, biuret, boronic acid, butyl, carbamate, carbine, carbinol, carbocyclyl, carbocyclylic, carbocycle, carbocyclo, carbodiimide, carbonate ester, carbonyl, carboxamide, carboxyl group, carboylic acid, chloroformate, crotyl, cumulene, cyanamide, cyanate, cyanate ester, cyanimide, cyanohydrin, cycloalkane, cycloalkene, cycloalkyne, cyclopropane, diazo, diazonium compound, diol, disulfide, enamine, enol, enol ether, enolate anion, enone, enyne, episulfide, epoxide, ester, ether, ethyl group, glycosidic bond, guanidine, halide, halohydrin, halogen, haloketone, hemiacetal, hemiaminal, heterocyclic group, heterocyclic, heterocycle, heterocyclyl, heterocyclo, heteroaryl, hydrazide, hydrazine, hydrazone, hydroperoxide, hydroxamic acid, hydroxyl, hydroxyl radical, hydroxylamine, hydroxymethyl, imine, iminium, isobutyramide, isocyanate, isocyanide, isopropyl, isothiocyanate, ketal, ketene, ketenimine, ketone, ketyl, lactam, lactol, mesylate, metal acetylide, methane, methoxy, methyl group, methylene, methylenedioxy, N-oxoammonium salt, nitrate, nitrile, nitrilimine, nitrite, nitro compound, nitroamine, nitronate, nitrone, nitronium ion, nitrosamine, nitroso, nitrosyl, nonaflate, organic peroxide, organosulfate, organosulfur compound, organophosphorous, organohalide, orthoester, osazone, oxime, oxon, pentyl, peptide, peroxide, persistent carbine, phenyl group, phenylene, phosphalkyne, phosphate, phosphinate, phosphine, phosphine oxide, phosphinite, phosphite, phosphonate, phosphonite, phosphonium, phosphorane, propargyl, propyl, propynyl, radical, Schiff base, selenol, selenocarboxylic acid, selenoether, selenonic acid, semicarbazide, semicarbazone, silyl enol ether, silyl ether, sulfide, sulfinic acid, sulfenic acid, sulfonamide, sulfonate, sulfonic acid, sulfonyl, sulfoxide, sulfuryl, tellurols, thial, thioacetal, thioaldehyde, thioamide, thiocarboxy, thiocaroxylic acid, thiocyanate, thioester, thioether, thioketal, thioketone, thiol, thiourea, tosyl, triazene, triflate, trifluoromethyl, trihalide, trimethylsilyl, triol, urea, vanillyl, vinyl, vinyl halide, xanthate, ylide, ynolate but is not limited to only these.

Unless otherwise specified in this document the term "chemical modifier" is intended to mean single or plurality of chemicals and/or biological(s) which to certain degrees selectively interacts with at least one targeted molecular geometry in at least one component of the sample. In addition, the chemical modifier may have one or more chiral center(s).

Unless otherwise specified in this document the term "targeted molecular geometry" is intended to mean the three dimensional arrangement of the atoms that constitute a molecule. The targeted molecular geometry can be: the entire molecule, one or more functional groups in the molecule, the geometric frame whereby different functional group combinations within a molecule set up a molecule's molecular geometry, the topology of the molecule, the steric effects in the molecule, linear, trigonal planar, tetrahedral, octahedral, pyramidal, bent, but not limited to only these.

Unless otherwise specified in this document the term "complementary molecular geometry" is intended to mean the molecular geometry of the chemical modifier is similar to the targeted molecular geometry to a degree in which the interaction between the component of the sample to be separated/resolved and the chemical modifier is selective to some extent over non-targeted molecular geometries. The complementary molecular geometry can be: the entire molecule, one or more functional groups in the molecule, the geometric frame whereby different functional group combinations within a molecule set up a molecule's molecular geometry, the topology of the molecule, the steric effects in the molecule, linear (planar), trigonal planar, tetrahedral, octahedral, pyramidal, bent, but not limited to only these.

In one particular aspect of the present invention, one or more chemical modifiers are infused into the drift gas stream and introduced into the ion mobility based spectrometer. During the collisions between one or more components of the sample and one or more chemical modifiers, these interactions are transient in nature. Most of the chemical modifier does not involve a derivatization of the component of the sample via a permanent covalent bond, such as that used in covalent synthesis,(however, in some specific cases; a covalent cluster of sample components and the non-conventional chemical modifier could be formed when adding the modifiers in the appropriate section of the ion mobility based spectrometer). The chemical modifier generally does not involve ion-molecule reactions such as the $S_N2$ nucleophilic displacement reactions of chloride anions with alkyl bromides in a nitrogen buffer gas [Giles, K., Grimsrud, E. P. J. Phys. Chem. 1992, 96, 6680-6687]. Instead, the chemical modifier involves ion-molecule interactions in the form of transient complexes such as hydrogen bonds, van der Waals forces, dipole-dipole, steric hindering effects, short-lived metastable, clusters, but not limited to only these. The clusters can be long-lived non-covalent interactions or covalent interactions. As the transient complexes formation and deformation process rapidly repeats in the ion mobility based spectrometer, a structure selective resolution of components of the sample can be observed. The contribution of the chemical modifier to the average measured mobility shift should be concentration dependent and analytically quantifiable. The degree of interaction between the components of the sample and the chemical modifiers can also be altered by altering the type and concentration of the chemical modifiers and gas temperature, pressure and flow rate in the drift tube. Multiple point interactions between sample and chemical modifier could potential result in more substantial mobility shift.

Figure 2:
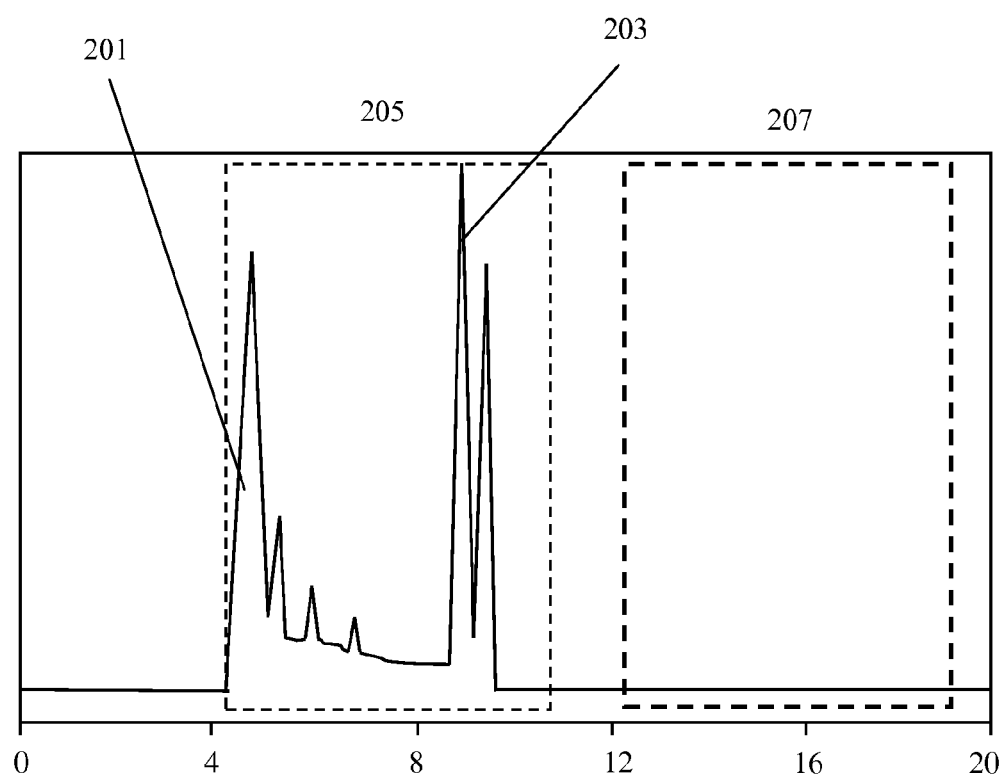
FIG. 2 shows the ion mobility spectrum of chemicals introduced into an ion mobility based spectrometer.

Certain embodiments of the present invention involve a series of chemical modifiers that selectively interact with the targeted molecular geometry of chemical agents or explosives resulting in a structure selective based drift time shift in the IMS. A drift gas chemical modifier can selectively increase nitro based compounds drift time according to the selected modifier's molecular geometry. In the following non-limiting example, the chemical modifier's targeted molecular geometry is to a nitro functional group. The drift time of nitro based explosives such as TNT, RDX, and Nitroglycerine all are moved away from their original drift time eliminating common interference problems in IMS through the use of designed gas phase ion chemistry. FIG. 2 shows an ion mobility spectrum resulting from a laboratory test in which a known amount of TNT was introduced to the system. During the course of detection, multiple peaks were detected and only one of them is directly related to the component TNT 203. Another predominant peak 201 is the instrument background ion. Note that there is significantly less or no interference existing in the relatively long drift time region 207. In this particular example, the several other interferant peaks distributed between these two peaks; most of them are in the low drift time range. In addition, this spectrum was acquired in a laboratory environment whereby field samples commonly show more complex ion mobility spectra. Unfortunately, most nitro based targeted analytes have very similar ion mobilities as the interferants. The nitro based explosives have a drift time in the region as shown within the 205 dashed line box in FIG. 2. In this region, detection windows and thresholds are a compromise between sensitivity and false alarm rate and significantly limit detecting low levels of explosives and make it impossible to detect explosives. A structure selective ion-molecular interaction (SSIMI) can be used to selectively adjust the drift time of components in a sample of interest, to a desired region of the IMS spectrum where few or no interfering chemicals exist. As FIG. 2 illustrates, if the drift time of all nitro based explosives is shifted the long drift time range 207 dashed line box, there is very low probability for interference; the detection threshold could be reduced to a much lower level.

The following examples are non-limiting. The targeted molecular geometry could be used for other similar ion-molecular interactions.

Figure 3:
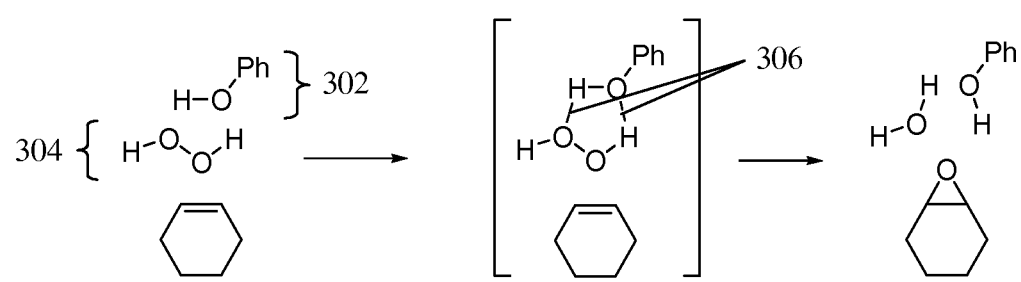
FIG. 3 shows the mechanism for the epoxidation of cyclohexene with hydrogen peroxide using phenol as a catalyst.
Figure 4:
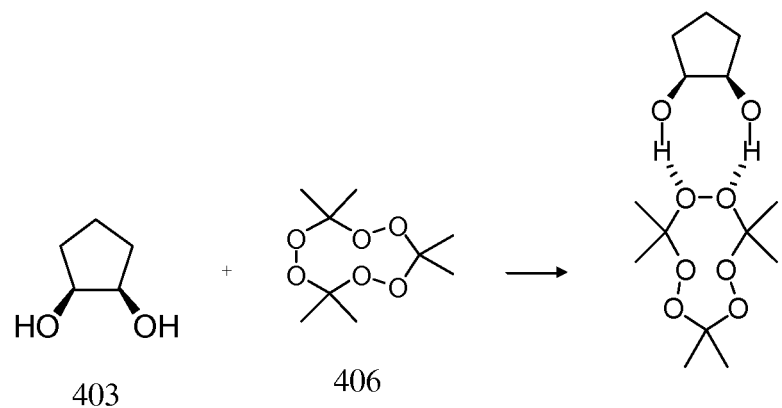
FIG. 4 shows the chemoselective interaction of the peroxide functional group in TATP with cyclopentanediol through hydrogen bonding.
Figure 5:
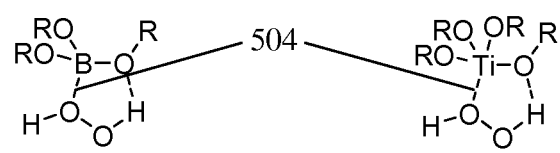
FIG. 5 shows hydrogen bonding with empty orbitals of boron and titanium.
Figure 6:
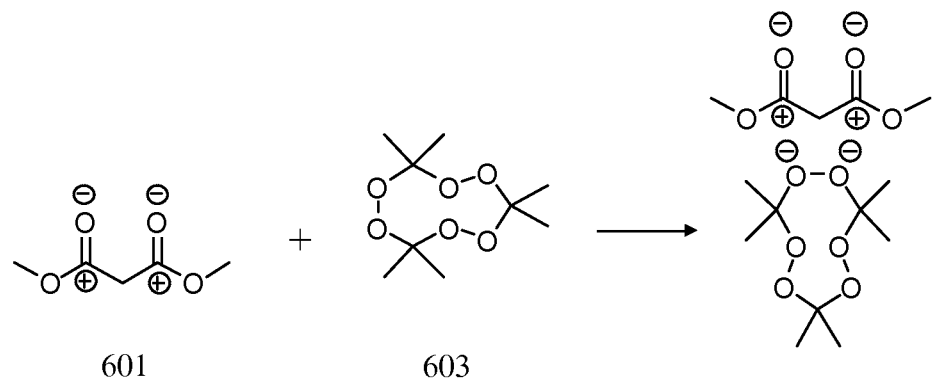
FIG. 6 shows a dipole-dipole interaction with TATP and dimethyl malonate.
Figure 12:
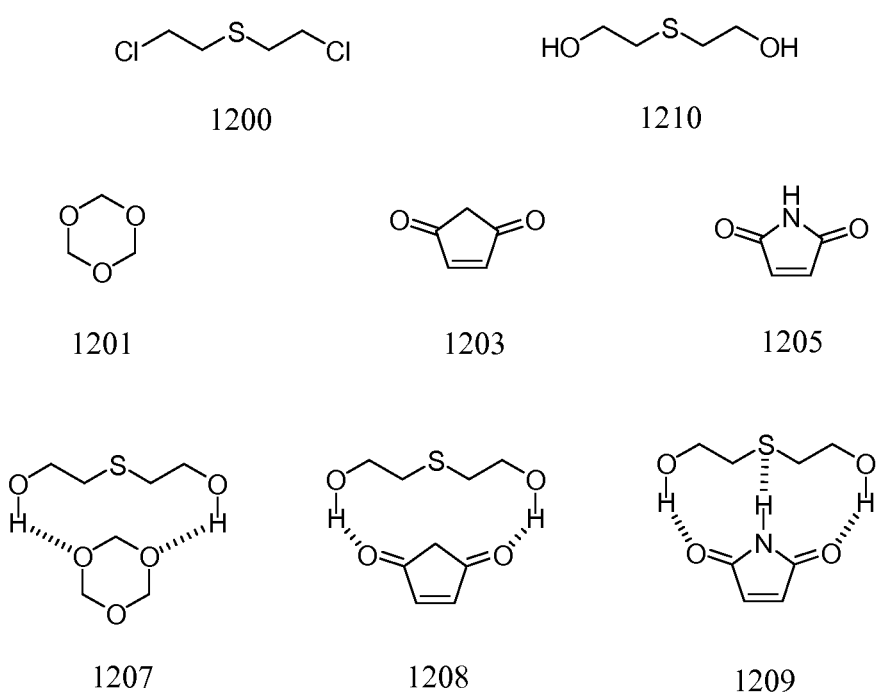
FIG. 12 shows hydrogen bonding interactions between chemical modifiers and degradation product.
Figure 13:
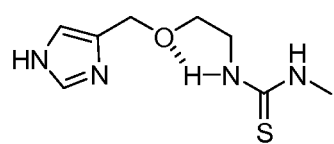
FIG. 13 shows an intramolecular hydrogen bonding that produces a conformationally restricted molecule.
Figures 14A, 14B:
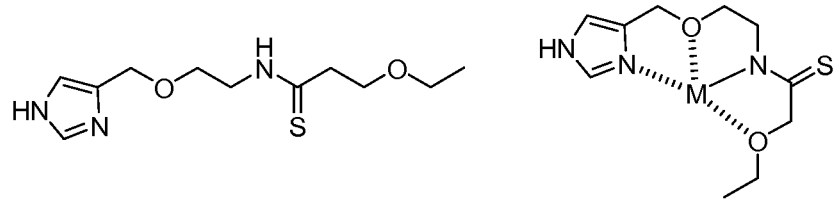
FIGS. 14A-B shows a unrestricted molecule FIG. 14A and a metal bound complex 14B.

Detecting peroxides and their precursors is very difficult for the existing ion mobility spectrometers. Current IMS based systems can detect the break down products of triacetonetriperoxide (TATP) but exhibit high false alarm rates in a short drift time detection window, and they are not able to detect hydrogen peroxide. To resolve the peroxide detection issue, several gas phase interaction mechanisms can be used to realize SSIMI. A hydrogen bonding interaction between a chemical modifier and the targeted molecular geometry of a peroxide functionality in TATP is the next non-limiting example. In organic synthesis, epoxidation of alkenes using hydrogen peroxide is typically accomplished by employing a metal catalyst. Recently, it has been shown that organic, non-metal compounds are capable of activating $H_2O_2$ for the epoxidation of olefins [J. Wahlen, D. E. De Vos, P. A. Jacobs, Org. Lett. 5, (2003) 1777-1780]. As shown in FIG. 3, Jacobs uses phenol 302 as the catalyst to activate hydrogen peroxide 304 through hydrogen bonding 306. The two reacting molecules must attain a specific geometry to permit hydrogen bonding to occur. This reaction demonstrates a strong interaction between phenol and hydrogen peroxide for epoxidation of cyclohexene to occur. By using this geometrically aligned hydrogen bonding interaction, the drift time of a hydrogen peroxide sample using phenol as a modified drift gas will shift the hydrogen peroxide sample to a longer drift time due to this hydrogen bonding interaction. Levels of chemical modifiers in the ppm range can cause drift times to shift by milliseconds. The amount of shift depends upon the strength of ion-molecular interaction forces, the degree of molecular complementary molecular geometry with the peroxide, modifier concentration, and operating parameters (such as temperature). Similarly, other chemical modifiers, such as perfluorinated alcohol solvents could also be used to achieve the effect of a structure selective interaction with peroxides [K. Neimann, R. Neumann, Org. Lett. 2, (2000) 2861-2863]. In addition, cis-1,2-cyclopentanediol 403 could be used to selectively interact with triacetone triperoxide (TATP) 406 using multiple point hydrogen bonding to shift the drift time of TATP to a range with less interference from other components in the sample as shown in FIG. 4. TATP has three peroxide functional groups taken together to form a ring. The molecular geometry of the peroxide functionality contained in the ring positions the lone pairs on each oxygen in a orientation such that two hydrogen bond donors would need to be in the same plane, such as that found in cis-1,2-cyclopentanediol 403. In addition to hydrogen bonding, elements with empty orbitals 504 and substituents that are hydrogen bond acceptors could be used to interact with electron rich peroxides such as those that are shown in FIG. 5. Some non-limiting examples are: oxophilic boron and titanium based modifiers such as $Ti(OEt)_4$, $Ti(i\text{-}OPr)_4$, $Ge(OMe)_4$, $B(OMe)_3$, $B(OEt)_3$ and $B(i\text{-}OPr)_3$, etc. can be used for their ability to interact with peroxide functionality in a variety of drift tube conditions. This group of modifiers has boiling points from 58 to 232° C. and are suitable to be introduced as a low concentration (ppm) vapor mixture in the drift gas. Another gas phase structure selective ion-molecular interaction that could be used is a dipole-dipole interaction. FIG. 6 shows the interaction between dimethyl malonate 601 and TATP 603. This non-limiting example demonstrates a two-point dipole-dipole interaction with a great degree of selectivity from being geometrically aligned. Dimethyl malonate is specifically chosen to match the molecular geometry and interact with the O—O functionality in TATP.

With a similar ion-molecular interaction illustrated for peroxides, the drift time of nitro based explosives could also be shifted. Some non-limiting examples are discussed for ion-molecular interaction forces, such as hydrogen bonding and a dipole-dipole interaction. FIG. 7 illustrates two possible hydrogen bonding schemes that demonstrate multiple interaction points between boric acid and nitro compounds. Nitro compounds contain one or more nitro functional groups. The nitro functional groups are "planar" structures, therefore boric acid is chosen because it's trigonal planar geometry which is complementary to the targeted molecular geometry.

FIG. 8 shows a dipole-dipole interaction of 2,5-Dimethylfuran 801 and an aromatic nitro compound 803 (e.g. TNT). In this interaction, the geometry of the modifier is critical for a successful drift time shift because the dipole-dipole interaction normally is a near range interaction. Divinyl ether 902 interacts with TNT 904 either in a side-to-side manner FIG. 9A or top-to-bottom manner FIG. 9B. The discussed examples are non-limiting, other molecules that have similar structural functionality and charge distribution can also be used as modifiers to shift drift time of nitro compounds.

Many other molecules can be used for the SSIMI method, such as, but not limited to the degradation products of nerve agents. FIG. 10 shows two possible degradation products of the VX/V-type nerve agent 1000, an amino alcohol 1001 and an amino thiol 1003, that can selectively interact with lewis acids since they are bidentate ligands. In addition, oxygen and sulfur have strong potential to interact with boron and titanium in a reversible fashion. As shown in FIG. 11, $Ti(OR)_4$ and $B(OR)_3$ can have strong reversible interactions with various molecules. Titanium isopropoxide and Germanium methoxide both have a complementary molecular geometry that is tetrahedral. Therefore, up to four functional groups on the targeted molecular geometry could interact in a tetrahedral geometry. The degradation products of sulfur mustard 1200 could selectively form hydrogen bonding with several modifiers, depending on the modifier's geometrical positioned functionality and strength of interaction. FIG. 12 shows the modifier structures, 1,3,5-Trioxane 1201, 4-Cyclopentene-1, 3-dione 1203, and Maleimide 1205, and the possible interactions 1207, 1208, & 1209 with degradation and product 1210 of the sulfur mustard 1200.

The SSIMI resolution/separation method can be used to identify biological molecules as well as chemicals. Trypsin is used to break down proteins. Hence it has been used widely in various biotechnological processes. Trypsin predominantly cleaves peptide chains at the carboxyl side of the amino acids lysine (Lys) and arginine (Arg), except when either is followed by proline. Trypsin is commonly used in biological research during proteomics experiments to digest proteins into peptides for mass spectrometry analysis, e.g. in-gel digestion. Trypsin is particularly suited for this, since it has a very well defined specificity, as it hydrolyzes only the peptide bonds in which the carbonyl group is contributed either by an Arg or Lys residue. The Arg or Lys functionality exposed in these peptides along with the carboxylic acid functionality at one end of the peptide produces a defined molecular geometry that a chemical modifier can be designed to selectively interact with. Since the Arg functionality is different than the Lys functionality and they both have different molecular geometries, then a chemical modifier can selectively interact with one over the other. For example, after a Trypsin digest, the researcher can add a chemical modifier to the IMS that selectively interacts with Arg peptide fragments of the protein. These Arg peptide fragments can be separated/resolved from the Lys peptide fragments and can be further identified by having an MS or other analytical instrument connected to the IMS.

In another set of embodiments of the present invention at least one targeted molecular geometry in at least one component of the sample to be resolved has at least one chiral center including one or more functional groups. The chiral center(s) can be: part of, attached to, adjacent to, removed from, and any combinations thereof, the functional group(s). At least one chemical modifier is added to the drift gas that interacts selectively with the targeted molecular geometry to be resolved. The chiral center(s) can set the molecular geometry to have a specific interaction with the chemical modifier, which may or may not include a chiral center(s).

In yet another set of embodiments of the present invention at least one immobilizing agent can be added to the sample to rigidify with: either the targeted chemical and/or biological molecules or the impurities and/or interferences in the sample, or both. The immobilizing agent can be added to the sample at various stages of the process of introducing the sample to the IMS. Some non-limiting examples of adding the immobilizing agent to the sample are: prior to adding the sample into the ionization region, while the sample is in the ionization region, after the sample has been ionized. As the molecules increase in molecular complexity (size, number of stereogenic centers, number of chiral centers, number of functional groups, etc) more conformations are possible due to the flexibility of the molecule, which can thus adopt multiple different conformations while traveling down the drift tube. By rigidifying the molecules, the immobilizing agent can limit the possible conformations of the components of the sample. The immobilizing agents include, but are not limited to: chemical and/or biological molecules, inorganic compounds, organic compounds, metals, minerals, macromolecules, polymers, biopolymers, nucleotides, proteins, carbohydrates, lipids, macrocycles, and nanotubes. Fewer conformations of the components of the sample can enhance resolution/separation owning to more specific interactions with the chemical modifier. At least one chemical modifier can selectively interact with the component and/or the associated immobilizing agent of the sample and resolve the component from other components of the sample based on their measured ion mobility characteristics. The measured ion mobility characteristic can be a measured drift time of the components. The measured ion mobility characteristic can be the ion flight path under influence of high field and/or low field conditions in an ion mobility base spectrometer. A non-limiting example of the process would be to form a [metal-sample component] complex prior to ionization and then perform the mobility analysis while adding at least one modifier to the drift gas. Interactions between the [metal-sample component] complex and the modifier would be identified by different drift times of the molecules on a detector. The detector may be a: mass spectrometer, faraday plate, CCD, high pressure multiplier, any transducer that produces a signal proportional to the number of ions at the detector, but not limited to only these.

Many different metals are envisioned to be used for forming a [metal-sample component] complex, including: Alkali metals (Li, Na, K, Rb, Cs, Fr), Alkaline earth metals (Be, Mg, Ca, Sr, Ba, Ra), Transition metals (Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Rf, Db, Sg, Bh, Hs, Uub), Metalloids (B, Si, Ge, As, Sb, Te, Po), other metals (Al, Ga, In, Sn, Tl, Pb, Bi), Lanthanides (La, Ce, Pr, Nd, Pm, Sm, Eu, Gd, Tb, Dy, Ho, Er, Tm, Yb, Lu), Actinides (Ac, Th, Pa, U, Np, Pu, Am, Cm, Bk, Cf, Es, Fm, Md, No, Lr), but not limited to only these. The metals could be used with various counter ions and/or combinations of counter ions including: Halogen (Cl, Br, I, F), acetate, nitrile, hydrate, acetylacetonate, carbonate, hydroxide, methoxide, ethoxide, propoxide, nitrate, oxide, perchlorate, selenide, sulfate, sufide, triflate, thiocyanate, but not limited to only these.

An ion mobility spectrometer can recognize separate structural (constitutional) or conformational isomers since they have a different geometric appearance but exactly the same mass. Ions with the same mass but with different collision cross sections have different mobilities. If different conformational isomers of the same compound are analyzed, the isomer with the smallest geometric cross section will have the highest ion mobility. It has been shown that tightly folded proteins have a smaller geometric cross section than the unfolded conformation of the same protein and the unfolded conformation therefore has a longer travel time to the detector. In small molecules, less than 500 MW, the free-energy difference between conformers (conformational free energy) can be a small or large rotational energy barrier depending on the molecules functional groups. In addition, functionality within the molecule can influence the molecules preferred conformation. For example, an intramolecular hydrogen bonding of the compound shown in FIG. 13 produces a conformationally restricted molecule.

One embodiment of this invention is to rigidify the molecules (limit the number of conformations) by adding a immobilizing agent to the sample prior to ionization. A non-limiting example is shown in FIGS. 14A-B, where a metal is added to the unrestricted molecule in FIG. 14A, which produces a metal complex as shown in FIG. 14B. The metal coordination complex can be formed by the interaction of atoms to the metal by action of one or more of: a metallic bond, a coordinate covalent bond, a ionic bond, or a combination of these, but not limited to only these interactions. By adding a metal to bind to functionality in a molecule which contains at least one chiral center, this would limit the molecule's conformations and optimal enantiodiscrimination would occur by the chemical modifier which may contain one or more chiral centers. One non-limiting example is shown in FIGS. 15A-15B. FIG. 15A shows a component of the sample with 2 chiral centers and multiple possible conformations. By adding a metal to the component before it is ionized in the IMS, the conformation shown in FIG. 15B may predominate and produce a rigid structure for optimal chemical modifier interaction.

In one aspect of the gas phase separation/resolution method is using an immobilizing agent to stabilize the gas phase structure of analytes in order to enhance the gas phase separation. In variety of embodiments, a reagent that can frame (affix) the higher order structure of a gas phase analyte molecule is used to achieve well-defined gas phase mobility of the analytes. Forming complexes with metals and/or other molecules is illustrated above as a non-limiting example of this method. In alternative embodiments, the analytes can be first affixed on a carrier, the carrier reagent can be a molecule, a particle, nanotube, or macromolecules, and then separate the analytes with different characteristics via above described SSIMI method. In some cases, when the analyte is affixed, certain active sites of the analytes may be accessible allowing designed gas phase interaction to occur in a well-defined manner. During the execution of this method, the interaction between the analytes and the carriers could either be permanent or in transient time. The immobilizing agents having a spatial structure that is used to reduce the degree of freedom of intramoleuclar movement of the component in the samples. The immobilizing agents limit conformational changes to the component of the sample such that the modifier interacts with a defined three dimensional structure of the component of the sample.

A structure selective resolution method, can comprise: adding at least one immobilizing agent to a sample, which rigidifies at least one component of the sample; ionizing and providing the sample with the immobilizing agent to an ion mobility based spectrometer; adding at least one chemical modifier that interacts selectively with the component and/or the associated immobilizing agent of the sample; and resolving the component from other components of the sample based on their measured ion mobility characteristics.

The immobilizing agents can include, but are not limited to: chemical and/or biological molecules, inorganic compounds, organic compounds, metals, minerals, macromolecules, polymers, biopolymers, nucleotides, proteins, carbohydrates, lipids, macrocycles, and/or nanotubes.

Another embodiment of this invention is to add at least one transforming agent to a sample, which bonds/binds (interacts) to at least one component of the sample. The bonding interactions or attraction forces may include; hydrogen bonds, van der Waals forces, dipole-dipole, steric hindering effects, coordinate covalent bond, metallic bond, ionic bond, non-covalent bond, covalent bond, weak covalent nature, antibonding, short-lived metastable, clusters, but is not limited to only these. The clusters can be long-lived non-covalent interactions and covalent interactions. The transforming agent can be added to the sample at various stages of the process of introducing the sample to the IMS. Some non-limiting examples of adding the transforming agent to the sample are: prior to adding the sample into the ionization region, while the sample is in the ionization region, after the sample has been ionized. At least one chemical modifier is added to the IMS that interacts selectively with the component of the sample and/or transforming agent which resolves/ separates the component from other components of the sample based on their measured ion mobility characteristics. The measured ion mobility characteristic can be a measured drift time of the components. The measured ion mobility characteristic can be the ion flight path under influence of high field and/or low field conditions in an ion mobility base spectrometer. The transforming agent is designed to selectively bond/bind to at least one functional group of the component to block these functional group(s) from interactions with the chemical modifier and/or is designed to interact with the chemical modifier after selectively bonding/binding to at least one functional group of the component. The first use of the transforming agent described above would be similar to how a protecting group is used in organic chemistry reactions to block or protect a functional group while reactions are carried out on other functional groups on the compound. As a non-limiting example, a component of the sample has a non-chiral bonding/binding functionality as well as a chiral bonding/binding functionality. In this situation, the non-chiral binding pocket/functionality could be avoided by a chiral chemical modifier and therefore enhance chiral recognition if a transforming agent was added to the sample which blocks the non-chiral binding pocket/functionality from interaction with the chiral chemical modifier. This would occur by selectively interacting with the sites of the targeted functionality near the chiral center of the molecule. A non-limiting example is shown in FIG. 16, where the molecule has one chiral center and multiple possible conformations. If a metal (a transforming agent) is added to the molecule it may bind in the manner shown in FIG. 17A, allowing a chiral modifier to interact in the vicinity of the molecule's chiral center, shown in FIG. 17B. By adding a complexing metal to the component of the sample, before the enantiodiscrimination process, the desired chiral recognition site is bound instead of unfavorable binding pocket(s) and/or functional group(s). FIG. 17C shows the chiral modifier interacting with a non-chiral binding pocket instead of interacting in a vicinity that is near the chiral center of the molecule. Described below is a non-limiting example for the second use of the transforming agent whereby the transforming agent is designed to interact with the chemical modifier after selectively bonding/binding to at least one functional group of the component. In this non-limiting example, a biologically active peroxide such as epiplakinic acid D 1801 (a component of the sample) shown in FIG. 18 does not contain functionality that interacts selectively with the chemical modifier 1805. Therefore, a transforming agent 1803 is added to the sample and bonds/binds to the peroxide functionality of epiplakinic acid D 1801 to some degree as shown in FIG. 19 as a complex 1901. The nitro functionality found on the transforming agent 1803 furnishes a handle to bond/bind with the chemical modifier 1805. FIG. 19 shows the chemical modifier bound selectively to the complex 1901 through the nitro functionality found on the transforming agent 1803 as complex 1903. In the above example the transforming agent 1803 bonds/binds to the epiplakinic acid D 1801 (the component of the sample) through non-covalent bonding (hydrogen bonding), however this method could also utilized by using transforming agents that covalently bonds to the component of the sample via a synthetic transformation (organic reaction).

A structure selective resolution method, can comprise: adding at least one transforming agent to a sample, which bonds to at least one component of the sample; ionizing and providing the sample with the transforming agent to an ion mobility based spectrometer; adding at least one chemical modifier that interacts selectively with the component of the sample and/or the transforming agent; and resolving the component from other components of the sample based on their measured ion mobility characteristics. The transforming agent can be designed to selectively bond to at least one functional group of the component to block said at least one functional group from interactions with the chemical modifier. The transforming agent can be designed to interact with the chemical modifier after selectively bonding to at least one functional group of the component.

Another embodiment of this invention is to use the immobilizing agent and transforming agent as one agent. In this case the agent rigidifies at least one component of the sample and the chemical modifier interacts selectively with the agent that rigidified the component of the sample. This is similar to the above described second use of the transforming agent, although in this case the transforming agent also rigidifies the component of the sample.

In yet another embodiment of this invention is to use the immobilizing agent and transforming agent together. In this case, the immobilizing agent added to the sample rigidifies at least one component of the sample and the transforming agent which is also added can be used to selectively bond/bind to at least one functional group of the component to block these functional group(s) from interactions with the chemical modifier and/or is designed to interact with the chemical modifier after selectively bonding/binding to at least one functional group of the component.

In yet another aspect of the present invention one or more internal and/or external standards (calibrants) can be used to calibrate the ion mobility base spectrometers by defining and/or knowing the degree of the interaction between modifiers and ions. Ion mobility charateractics of the calibrants, such as the drift time, in the ion mobility spectrum can be used to verify the system readiness. The standards can be a substance that has known degree of interaction with the modifiers. These calibrants can be used with any of the disclosed methods in this document that utilize chemical modifers as well as other ion mobility based spectrometers that may not use a chemical modifier. With the understanding of the relationship the ion mobility behavior of a sample component under a variety of operating conditions, such as, but not limited to, temperature, pressure, humidity, electric field, flow rate, the kind of modifiers, modifier concentration, etc., a calibration standard can be used to determine the operating condition changes and predict associated change of ion mobility characteristics, such as ion drift time. In a variety of embodiments, the calibration method may consist of introducing a first calbrant and measuring a first ion mobility characteristic; introducing a second calibrant and measuring the second ion mobility characteristic; using measured ion mobility characteristics to determine proper instrument operating parameters, such as, but not limited to, temperature, pressure, humidity, electric field, flow rate, the kind of modifiers, modifier concentration, etc. The system calibration process may also include using the calibration parameters that correlate known and unknown instrument operational condition to correct data obtained under unknown instrument conditions. Such correction can either been done on-the-fly or after the data is obtained. In many embodiments, the correction can be achieved using system control and data acquisition software and/or data analysis software. In practice, the first and second calibrant can be introduced to the instrument either sequentially or simultaneously. For above described calibration process, one or more calibrants are used. In addition, the calibrant can have more than one peak in the spectrum that can be used for identification purposes.

What is claimed is:

1. A structure selective resolution method, comprising:
    a) providing a sample with at least one component having a targeted molecular geometry with at least one chiral center to an ion mobility based spectrometer;
    b) ionizing the sample;
    c) adding at least one chemical modifier having a complementary molecular geometry that interacts selectively with the targeted molecular geometry of said at least one component of the sample;
    d) resolving at least one component from the other components of the sample based on their measured ion mobility characteristics; and
    e) correlating the ion mobility characteristic under different operating conditions using a calibration method.

2. The structure selective resolution method of claim 1, wherein the measured ion mobility characteristic is a measured drift time of the components.

3. The structure selective resolution method of claim 1, wherein the measured ion mobility characteristic is the ion flight path under influence of high field and/or low field conditions in an ion mobility base spectrometer.

4. The structure selective resolution method of claim 1, wherein the complementary and/or targeted molecular geometry is: linear (planar), trigonal planar, or bent.

5. The structure selective resolution method of claim 1, wherein the complementary and/or targeted molecular geometry is: tetrahedral, octahedral, or pyramidal.

6. The structure selective resolution method of claim 1, wherein the complementary and/or targeted molecular geometry is: the entire molecule, one or more functional groups in the molecule, the geometric frame, or the topology of the molecule.

7. The structure selective resolution method of claim 1, wherein said at least one chemical modifier comprises at least one chiral center.

8. The structure selective resolution method of claim 1, wherein said at least one component of the sample comprises: explosives, chemical warfare agents, toxic industrial chemicals, toxins, biological warfare agents and/or other chemical, biological compounds.

9. The structure selective resolution method of claim 1, wherein said at least one chemical modifier is added to the sample prior to ionization and/or directly into a ionization source, reaction region, drift region of a drift tube.

10. The structure selective resolution method of claim 1, wherein the component of the sample that the chemical modifier interacts preferentially with are a impurity(ies) and/or interference(s) in the sample.

11. A structure selective resolution method, comprising:
    a) adding at least one immobilizing agent to a sample, which limits the number of conformations of the sample and rigidifies at least one component of the sample;
    b) ionizing and providing the sample with the immobilizing agent to an ion mobility based spectrometer;
    c) adding at least one chemical modifier that interacts selectively with the component and/or the associated immobilizing agent of the sample; and
    d) resolving the component from other components of the sample based on their measured ion mobility characteristics.

12. The structure selective resolution method of claim 11, wherein the immobilizing agent is a metal or a mineral.

13. The structure selective resolution method of claim 11, wherein the immobilizing agent is a molecule, a particle, a nanotube, or a macromolecule.

14. The structure selective resolution method of claim 11, wherein the immobilizing agent is a biological molecule, a nucleotide, a protein, a carbohydrate, or a lipid.

15. The structure selective resolution method of claim 11, wherein the immobilizing agent is a polymer or a biopolymer.

16. A structure selective resolution method, comprising:
a) adding at least one transforming agent to a sample, which bonds to at least one component of the sample;
b) ionizing and providing the sample with the transforming agent to an ion mobility based spectrometer;
c) adding at least one chemical modifier that interacts selectively with the component of the sample and/or the transforming agent; and
d) resolving the component from other components of the sample based on their measured ion mobility characteristics.

17. The structure selective resolution method of claim 16, wherein the transforming agent is designed to selectively bond to at least one functional group of the component to block said at least one functional group from interactions with the chemical modifier.

18. The structure selective resolution method of claim 17, further comprises adding at least one immobilizing agent to a sample, which rigidifies at least one component of the sample.

19. The structure selective resolution method of claim 16, wherein the transforming agent is designed to interact with the chemical modifier after selectively bonding to at least one functional group of the component.

20. The structure selective resolution method of claim 16, wherein the transforming agent also rigidifies the component of the sample.

* * * * *